United States Patent [19]

Behmann

[11] Patent Number: 4,775,794
[45] Date of Patent: Oct. 4, 1988

[54] PROCESS AND APPARATUS FOR MEASUREMENT OF LIGHT-ABSORBABLE COMPONENTS DISSOLVED IN LIQUIDS

[75] Inventor: Henry Behmann, Puslinch, Ontario, Canada

[73] Assignee: Zenon Environmental Inc., Burlington, Ontario, Canada

[21] Appl. No.: 115,314

[22] Filed: Nov. 2, 1987

[51] Int. Cl.$^4$ .............................................. G01J 1/42
[52] U.S. Cl. ................................... 250/373; 250/435
[58] Field of Search ................... 250/372, 373, 432 R, 250/435; 356/51, 436, 440; 422/24

[56] References Cited

U.S. PATENT DOCUMENTS 4,304,996 12/1981 Blades ................................ 250/373

Primary Examiner—Eugene R. LaRoche
Assistant Examiner—David Mis
Attorney, Agent, or Firm—Rogers & Scott

[57] ABSTRACT

The invention provides a new method and apparatus for measuring the concentration of ultra-violet light absorbing organic materials liquids, particularly in pure or ultra-pure water, the speed and convenience being such that it is possible to take successive readings with periods as short as ten seconds. The apparatus can be mounted directly in or as a by-pass to a process stream, giving the capability of constant monitoring with virtually instant microprocessor-controlled response to measurements outside a pre-set range. The water to be measured passes upwards in a cylindrical opaque-walled sample cell at the upper end of which is mounted an intense light source, preferably a Xenon flash tube, and at the lower end of which is mounted two transmission photodetectors, which have in front of them respective narrow-band optical transmission filters in the ultra-violet and visible regions. The light source sits on the upper end of a quartz rod which extends into the cell at or below the water inlet and is coaxial with the cell longitudinal axis, the rod serving to direct the light toward the transmission photodetectors. The output from the "visible" photodetector is used to correct the output from the "ultraviolet" photodetector for transmission losses caused by particulates, element fouling and bubbles in the stream. Two reference photodetectors employing two similar transmission filters are disposed close to the flash tube outlet window and their signals are used to correct for variation in the flash tube output.

18 Claims, 16 Drawing Sheets

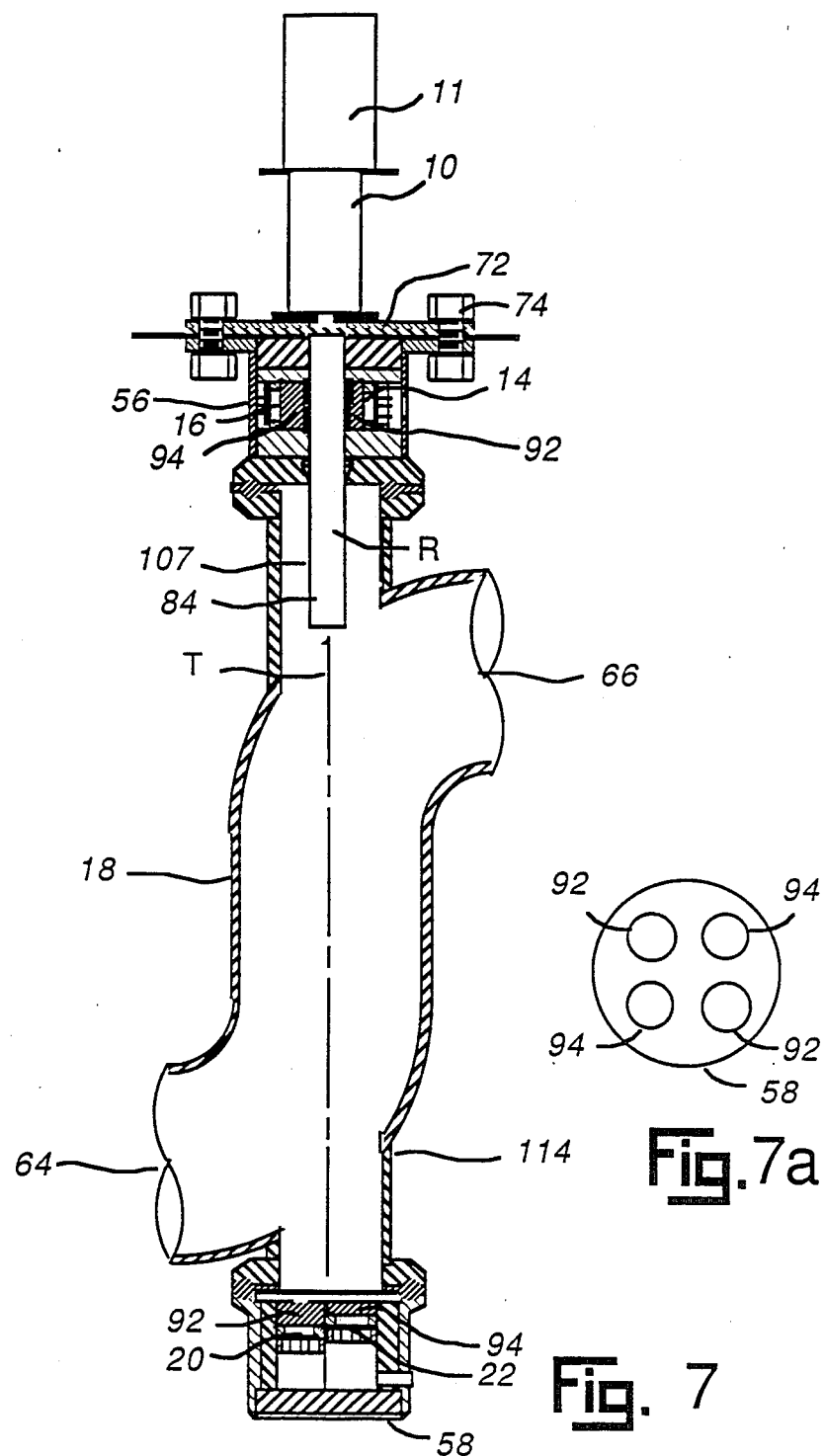

Fig. 8: Program Listing                          Page 1 of 9

( TIMER FOR THE 100^2 RUNS IN 1/100TH OF A SECOND TICKS
870522HB )
```
       HEX
 5     0 VARIABLE TIMER1
       0 VARIABLE TIMER2
       0 VARIABLE TIMER3
       0 VARIABLE TIMER4

10     CODE IRQRTN
           1C BIT,    ( CLEAR TIMER INTERRUPT )
           TIMER1 INC,
           0=
           IF,
15            TIMER1 1+ INC,
           THEN,
           TIMER2 INC,
           0=
           IF,
20            TIMER2 1+ INC,
           THEN,
           TIMER3 INC,
           0=
           IF,
25            TIMER3 1+ INC,
           THEN,
           TIMER4 INC,
           0=
           IF,
30            TIMER4 1+ INC,
           THEN,
           RTI,
       END-CODE

35     : IRQINIT
           [ DECIMAL ] 20000 [ HEX ] 1C !
           [ ' IRQRTN @ ] LITERAL IRQVEC ! 20 IER C!
           0 TIMER1 ! 0 TIMER2 ! 0 TIMER3 ! 0 TIMER4 ! ;

40     DECIMAL
       : 10S? ( --- f -CHECKS IF 10 SECONDS ELAPSED ON TIMER1 )
           1000 TIMER1 @ < DUP IF 0 TIMER1 ! THEN ;

: 1KS? ( --- f CHECKS FOR 1 SECOND ELAPSED ON TIMER2 )
45         100 TIMER2 @ < DUP IF 0 TIMER2 ! THEN ;
```

Fig. 8: Program Listing

```
        ( WORDS TO READ THE ANALOG VOLTAGE ON THE V/F *****)
        HEX
 5      : TRIGGER PB 40 ;

: RSET PB 20 ;

: ON   ( A,B --- )    ( SINGLE BIT ON )
10        OVER C@ OR SWAP C! ;

: OFF  ( A,B --- )    ( SINGLE BIT OFF )
            FF XOR OVER C@ AND SWAP C! ;

15      : SHOW  ( A,B --- F )   ( SINGLE BIT STATUS )
            SWAP C@ AND ;

DECIMAL
        10000 VARIABLE COUNTS    ( LOOP COUNT FOR DELAY1 )
20      0    VARIABLE DCOUNTS

: CREAT <BUILDS DOES> ; ( NON-VOL RAM VARIABLE BUILDER)

: TABLE <BUILDS DOES> SWAP 2 * + @ ; ( VECTOR BUILDER)
25
        CODE DELAY1
            COUNTS LDA,
            DCOUNTS STA,
            COUNTS 1+ LDA,
30          DCOUNTS 1+ STA,
            BEGIN,
              BEGIN, DCOUNTS DEC, 0= UNTIL,
              DCOUNTS 1+ DEC, 0=
            UNTIL,
35          NEXT JMP,
        END-CODE

: RESET RSET ON RSET OFF 1 0 DO LOOP  RSET ON ;

40      : ADCHAN  ( N1 --- ) ( SELECTS A CHANNEL, 0 TO 7 )
            PB C@ F8 AND OR PB C! ;

: TSETUP  ( --- )  ( COUNTER SETUP FOR V/F PULSES )
            MCR C@ 8 OR MCR C! ;
45
```

Fig. 8: Program Listing                                    Page 3 of 9

```
    : TSTART  ( -- ) ( COUNTER RESET AND START )
        INTFLG 7 ON FF 1C C! FF 1D C! FF 1E C! ;

: TSTOP  ( -- N1 ) ( COUNTER STOP AND READ )
5       1C C@ 1D C@ INTFLG 7 OFF E0 MCR C! IRQINIT 100 * + 0 SWAP - ;

: A/DREAD ( N1 -- N2 ) ( READ A/D CHANNEL )
        ADCHAN TSETUP TSTART DELAY1 DELAY1 TSTOP ;

10  ( ***** WORD TO MANIPULATE THE DAC08 ***** )

HEX
    : VOUT  PE C! ; ( B -SEND VALUE TO D/A FOR VOLT OUTPUT)

15  ( ***** DATA AQUISITION WORDS ***** )

DECIMAL

: ADJUST1  ( n1 n2 n3 n4 -- n3 n4 n1 n2 )
20      4 PICK 4 PICK >R >R >R >R 2DROP R> R> R> R> ;

: ADJUST  ( N1 N2 N3 N4 -- N2 N1 N4 N3 )
        SWAP >R >R SWAP R> R> ;

25  : TTRIG  ( -- ) ( TRIGGER FLASH )
        TRIGGER ON TRIGGER OFF TRIGGER ON ;

: SENSREAD ( -- N1,N2,N3,N4 READ FIRST 4 A/D CHANNELS)
        RESET TTRIG 4 0 DO I A/DREAD LOOP ADJUST ;
30
    : SEC  ( -- ) ( DELAY 1 SECOND )
        20000 0 DO LOOP ;

: SECS  ( N -- ) ( VARIABLE DELAY )
35      0 DO SEC LOOP ;

: .S4  ( N1,N2,N3,N4 --- N1,N2,N3,N4 )
    ( NON-DESTRUCTIVE PRINT OF 4 TOP STACK ITEMS)
        DECIMAL
40      CR DUP .
        OVER .
        3 PICK .
        4 PICK .
        5 SPACES ;
45
```

Fig. 8: Program Listing                          Page 4 of 9

```
    : RREADS  ( N — DATA ACQ CYCLE AND PRINT RAW DATA )
        0 DO SENSREAD CR .... 6 SECS LOOP ;

: FREADS 100 RREADS ;
5
    ( ***** WORDS TO CONTROL HITACHI LCD DISPLAY ***** )

DECIMAL

10  : MODESW PF 16 ; ( — A,B  ADDR & MASK FOR SWITCH #1 )

: UPSW  PF  8 ; ( — A,B  ADDR & MASK FOR SWITCH #2 )

: DOWNSW  PF 32 ; ( — A,B ADDR & MASK FOR SWITCH #3 )
15
    : HDSTROBE PF  1 ; ( — A,B ADDR & MASK FOR LCD STROBE)

: DDATA PG ; ( — A ADDR FOR DISPLAY DATA REGISTER )

20  HEX

0 VARIABLE ERRNO   ( ERROR NUMBER )

: TICK  HDSTROBE ON ; ( — )
25
    : TOCK  HDSTROBE OFF ; ( — )

: DATAREG  PF 2 ON ; ( — )

30  : .DATA  DATAREG TICK PG C! TOCK ; ( b — )

: CONTREG PF 2 OFF ;   ( — )

: .CONT CONTREG TICK PG C! TOCK ; ( b — )
35
    : HDINIT   ( — )
      30 .CONT
      200 0 DO LOOP
      30 .CONT
40    40 0 DO LOOP
      30 .CONT
      C .CONT
      6 .CONT ;

45  : HDCLEAR 1 .CONT 100 0 DO LOOP ; ( — )
```

Fig. 8: Program Listing

```
     : HDEMIT .DATA ; ( c -- )

: HDTYPE    ( addr n -- )
5      HDCLEAR -DUP
       IF OVER + SWAP
         DO I C@ HDEMIT LOOP
       ELSE DROP
       THEN ;
10
     : (.HD")    ( -- )
       R COUNT DUP 1+ R> + >R HDTYPE ;

: .HD"    ( -- )
15     22 STATE @
       IF COMPILE (.HD") WORD HERE C@ 1+ ALLOT
       ELSE WORD HERE COUNT HDTYPE
       THEN ;  IMMEDIATE

20   DECIMAL
     : ZEN
       .HD" *ZENON*"  30000 0 DO LOOP
       .HD" ORGANICS"  30000 0 DO LOOP
       .HD" MONITOR"  30000 0 DO LOOP
25     .HD" ZOM"  30000 0 DO LOOP ;

: .PPB    ( n -- )
       S->D SWAP OVER DABS <#
       66 HOLD 80 HOLD 80 HOLD 32 HOLD
30     # # # # #>
       HDTYPE DROP ;

: .PPM
       10 /
35     S->D SWAP OVER DABS <#
       77 HOLD 80 HOLD 80 HOLD 32 HOLD
       # # 46 HOLD # #>
       HDTYPE DROP ;

40   : .TOC    ( n -- )
       DUP 1000 <
       IF .PPB
       ELSE .PPM
       THEN ;
45
```

Fig. 8: Program Listing                    Page 6 of 9

( *** BASE 2 LOGARITHMS 5 PLACE *** )

DECIMAL

5   : RTSHIFT  2 / ;   ( N1 — N2 )

: TABLE
       <BUILDS DOES> SWAP 1 - 2 * + @ ;

10  -1    VARIABLE CHAR
    0     VARIABLE SHIFT-COUNT
    1     VARIABLE SHIFT-DIVISOR
    16384 CONSTANT ?TOO-BIG

15  TABLE FACTOR-LOG2
    10000 , 4000 ,
     1926 ,  931 ,
      458 ,  227 ,
      113 ,
20
    : CHARACTERISTIC
       DUP -1 CHAR !
       BEGIN
         1 CHAR +!
25       RTSHIFT
         DUP 0=
       UNTIL
       DROP ;

30  : LEFT-ALIGN
       14 CHAR @ -
       0 DO
       DUP + LOOP ;

35  : UPDATE-INDICES
       1 SHIFT-COUNT +!
       SHIFT-DIVISOR @ DUP +
       SHIFT-DIVISOR ! ;

40  : SHIFT-STEP
       DUP SHIFT-DIVISOR @
       1 SWAP */ NEGATE + ;

: CHECK-SHIFT
45     DUP ?TOO-BIG < ;

Fig. 8: Program Listing

```
     : NEW-COFACTOR
        IF DROP 0
        ELSE SWAP DROP 1
 5      THEN ;

: FACTOR2
        DUP SHIFT-STEP
        CHECK-SHIFT NEW-COFACTOR ;
10
     : INIT'IZE-MANT2
        0 SHIFT-COUNT !
        1 SHIFT-DIVISOR !
        0 SWAP ;
15
     : MANT2-SETUP
        CHARACTERISTIC
        LEFT-ALIGN ;

20   : DBL/LN
        13436 10000 */ ;

: LEFT-OVERS
        ?TOO-BIG -
25      DBL/LN + ;

: MANTISSA2
        INIT'IZE-MANT2 MANT2-SETUP
        7 0
30      DO
           UPDATE-INDICES
           BEGIN FACTOR2
           WHILE SHIFT-COUNT @
             FACTOR-LOG2
35         SWAP >R
           + R>
           REPEAT
        LOOP
        LEFT-OVERS ;
40
     : LOG2
        DUP DUP 0 SWAP <
        ROT ?TOO-BIG < AND
        IF
45       MANTISSA2 CHAR @
```

Fig. 8: Program Listing    Page 8 of 9

```
       ELSE
         DROP 0 0
       THEN ;

5   : LOG10 ( N1,N2---N3 CONVERTS CHAR & MANTISSA OF LOG2 )
       LOG2 1000 * SWAP 10 / + 3010 10000 */ ;

CREAT ZERO-S220 2000 , ( NVRV-ZERO ABSORB @ 220 SAMPLE)
     CREAT INF-S220 20 ,   ( NVRV-INFNITE ABSORB @ 220 SAMPLE)
     CREAT ZERO-S550 2600 , ( NVRV-ZERO ABSORB @ 550 SAMPLE)
10   CREAT ZERO-R220 2500 , ( NVRV -ZERO ABSORB AT 220 REF )
     CREAT INF-R220 20 ,   ( NRVR INFNITE ABSORB @ 220 REF )
     CREAT ZERO-R550 2500 , ( NRVR -ZERO ABSORB AT 550 REF )
     CREAT CALFACTOR 64 ,  ( NVRV - ABSORB TO CONC FACTOR )

15   0 VARIABLE OLDAV   ( PREVIOUS AVERAGE )

CREAT LAMBDA 70 ,   ( NVRV - AVERAGING FACTOR )

: 4SCALE ( N1,N2 --- N3 CONVERTS RATIO TO LOG10*1000 )
20     10000 SWAP */ LOG10 ;

: POW1    ( N1 -- N2 )    ( POWER OF SENSOR 1 )
         ZERO-S550 @
         DUP ROT MIN SWAP 4SCALE ;
25
     : POW2    ( N1 -- N2 )    ( POWER OF SENSOR 2 )
         INF-S220 @
         DUP ROT MAX SWAP -
         ZERO-S220 @
30       INF-S220 @ -
         DUP ROT MIN
         SWAP 4SCALE ;

: POW3    ( N1 -- N2 )    ( POWER OF SENSOR 3 )
35       ZERO-R550 @
         DUP ROT MIN SWAP 4SCALE ;

: POW4    ( N1 -- N2 )    ( POWER OF SENSOR 4 )
         INF-R220 @
40       DUP ROT MAX SWAP -
         ZERO-R220 @
         INF-R220 @ -
         DUP ROT MIN
         SWAP 4SCALE ;
```

Fig. 8: Program Listing

```
    : ABSORB1   ( N1,N2,N3,N4 --- N5 CALCULATE ABSORBANCE )
       POW4 SWAP POW3
       ROT POW2 +
5      SWAP ROT POW1 + SWAP - ;

: CALCALC   ( N1 --- N2 CONVERT TO CONCENTRATION )
       25 + CALFACTOR @ 100 */ ;

10  : AVG   ( N1 --- N2  CALCULATE NEW AVERAGE )
       OLDAV @ LAMBDA @ DUP
       ROT 100 */ 100 ROT -
       ROT 100 */ +
       DUP OLDAV ! ;
15
    : RUN   ( --- APPLICATION WORD FOR ZOM )
       HDINIT
       ZEN
       IRQINIT
20     BEGIN
         10S? IF
           SENSREAD .S4
           ABSORB1 DUP .
           0 MAX CALCALC DUP .
25         AVG ( 10 / DUP VOUT 10 * )
           DUP . .TOC
         THEN
         ?TERMINAL
       UNTIL ;
```

PROCESS AND APPARATUS FOR MEASUREMENT OF LIGHT-ABSORBABLE COMPONENTS DISSOLVED IN LIQUIDS

FIELD OF THE INVENTION

The present invention is concerned with processes and apparatus for the measurement of the light-absorbable components dissolved in liquids, and especially to such processes and apparatus which permit measurement and "on-line" monitoring of the organics content of water.

DESCRIPTION OF RELATED ART

The "quality" of purified liquids, particularly water is a relatively subjective characterisitic depending on the application for which the liquid has been purified, and can require the measurement of the dissolved inorganic materials (salts), suspended particulate material (cloudiness or turbidity), bacterial and pyrogenic content, and the dissolved organic compounds. One or all of these measurements may be considered important for the specific application under consideration. Generally, previously the only measurement which was formally considered broadly practical for water was that of conductivity (or its inverse measurement-resistivity). This non-specific measurement has been available using on-line instrumentation for many years, and for many applications is still an adequate measure of purity. Over the last several years there has been a growing awareness of the deleterious effects of dissolved organic compounds on certain industrial processes, particularly in the fields of electronics and pharmaceuticals. There has also been a realisation that the various treatment processes used to purify water do not usually remove the various types of impurities in similar proportions, i.e. a process which removes dissolved salts very well may not be very effective in removing small non-polar organic compounds. In such a case it is important to measure both the inorganic and organic contents of the water independently to gain a better appreciation of the overall product water quality. It is also found that the concentration of toxic organic chemicals generally is increasing, especially in industrial areas, and water which formerly was acceptably purified and therefore monitored only by resistivity, may now no longer be adequately pure.

Constant assurance of acceptable purity may be required, and is obtained by continuously, or at least frequently, monitoring the impurity content of the treated water. Hitherto this type of measurement has only been possible by the use of laboratory style analytical instruments or expensive and complex on-line apparatus. A measurement which is representative of organics content, and which is very analogous to conductivity is Total Organic Carbon (TOC), and this measurement can be performed in several different ways, each of which has been implemented in the form of a commercial instrument by one or more companies. However, all of this type of instrument of which I am aware have practical limitations in, for example, measurement response time, typically requiring five to ten minutes to obtain a reading; or the need to use chemical reagents; or the need for frequent re-calibration; or lack of robustness in construction; in some cases lack of sensitivity; and generally in high cost of production and operation.

Another type of instrument which is sometimes used to measure the organics content of water is a spectrophotometer, which usually has been adjusted to measure the absorption of 254 nanometer (nm) UV light emitted by a low pressure mercury lamp. The limitation of this type is two-fold, in that there are many organic substances which exhibit little or no absorption at 254 nm, and inorganic or colored substances in the water tend to interfere with the measurement and result in inappropriately high responses. It has also tended to be inadequately sensitive for measurements with ultrapure water, in which TOC's of less than 100 parts per billion (ppb) may be observed.

There are two further types of apparatus generally available in the marketplace for organics measurements. The first of these includes products such as the Xertex Model COA-1000 and Anatel Model A-100; these instruments operate on the principle that organics exposed to ultra-violet light will oxidize to form carbon dioxide, which in turn dissolves in water to form carbonic acid. When the fluid containing the organics of interest is ultrapure water, the resulting change in the conductivity becomes a direct indication of the oxidizable organic content. However the sensitivity of the method becomes unacceptably low when the conductivity is above 0.1 microsiemens. This is because the conductivity associated with other impurities in the water overwhelms the portion associated with the oxidized organics.

The second category is also available from several suppliers including Xertex (Dohrmann) and oxidizes by a number of different means the organic compounds in the water sample to $CO_2$, which is reduced to methane. The methane is generated in proportion to the concentration or oxidizable carbon in the sample, the amount of methane being detected by a flame ionization detector. This is probably the most generally used method for analyzing for total organic carbon (TOC), but the apparatus is complicated and is able to handle only small volume samples. The method also requires frequent calibration, reagents, purification of the methane gas, and cooling water. It is therefore relatively expensive to implement. Another method used by O.I.C. Corporation and others employs an expensive ultra-red detector to measure $CO_2$ produced from the organic compounds by an oxidation process.

In contrast to the above-described prior methods and apparatus, the method and apparatus of the present invention work with a wide range of potable and purified water; they provide a lower detection limit than most other UV absorbance methods (less than 10 ppb) and they do not require the addition of chemicals, or the use of cooling streams, gases or other auxiliary input. The apparatus can be made in robust form and requires only infrequent calibration, little or no routine maintenance when used in clean fluids, and it can be used with large volume continuous flow samples at flow rates in excess of 400 Lpm (by employment of a suitable sample cell). The response time of the apparatus can be adjusted to provide alarm indications in less than 10 seconds; and the cost to manufacture a typical unit, even in small runs, is commercially very acceptable.

DEFINITION OF THE INVENTION

It is a principal object of the invention therefore to provide a new method and apparatus for the measurement of the concentration in water of organic material that is ultra-violet light absorbent.

It is a more specific object to provide such apparatus that can readily be employed in conjuction with a process stream of water in order to monitor the concentration of the organics content thereof.

In accordance with the present invention there is provided an apparatus for determining the concentration of ultra-violet light absorbing organic substances in a liquid sample, the apparatus comprising:

a sample chamber for the reception of the liquid sample and having a longitudinal axis;

a light source positioned for its light to enter the sample chamber and when energised emitting light in two spaced spectrum portions, one of which is in the ultra-violet region and the other of which is in the visible region;

two transmission photodetectors positioned to receive light from the source that has passed through the sample chamber and the liquid sample along the longitudinal axis, one of the photodetectors being responsive to light in the said ultra-violet region and the other being responsive to light in the said visible region, the two photodetectors generating respective transmission ultra-violet and visible electric signals;

two reference photodetectors positioned to receive light from the source prior to it passing through the sample chamber, one of the photodetectors being responsive to light in the said ultra-violet region and the other being responsive to light in the said visible region, the two photodetectors generating respective reference ultra-violet and visible electric signals; and circuit means combining said electric signals to produce an output electric signal representative of the concentration of ultra-violet light absorbing substances in the liquid sample, in which the reference signals are employed to correct the transmission electric signal for variations in the light source light output, and in which the transmission visible electric signal is employed to correct the transmission ultra-violet electric signal for variations in the light transmission path.

Also in accordance with the present invention there is provided a method for determining the concentration of ultra-violet light absorbing organic substances in a liquid sample, the method comprising the steps of:

a. providing a sample chamber for the reception of the liquid sample and having a longitudinal axis;

b. positioning a light source for its light to enter the sample chamber and when energised emit light in two spaced spectrum portions, one of which is in the ultra-violet region and the other of which is in the visible region;

c. positioning two transmission photodetectors to receive light from the source that has passed through the sample chamber and the liquid sample along the longitudinal axis, one of the photodetectors being responsive to light in the said ultra-violet region and the other being responsive to light in the said visible region, the two photodetectors generating respective transmission ultra-violet and visible electric signals;

d. positioning two reference photodetectors to receive light from the source prior to it passing through the sample chamber, one of the photodetectors being responsive to light in the said ultra-violet region and the other being responsive to light in the said visible region, the two photodetectors generating respective reference ultra-violet and visible electric signals; and e. supplying the said electric signals to circuit means which combine them to produce an output electric signal representative of the concentration of ultra-violet light absorbing substances in the liquid sample, in which the reference signals are employed to correct the transmission electric signal for variations in the light source light output, and in which the transmission visible electric signal is employed to correct the transmission ultra-violet electric signal for variations in the light transmission path.

DESCRIPTION OF THE DRAWINGS

Processes and apparatus which are specific embodiments of the invention will now be described, by way of example, with reference to the accompanying drawings wherein:

FIG. 7 is a longitudinal cross-section through a second embodiment to show the application of the invention to a process stream, and also to show the use of multiple transmission photo-detectors;

FIG. 7a is a plan view of the multiple photo-detector assembly of FIG. 7; and

FIG. 8 is a listing of the program employed to control the microcomputer employed for automatic sequential operation of the apparatus.

DESCRIPTION OF THE PREFERRED EMBODIMENTS

Figure 1:
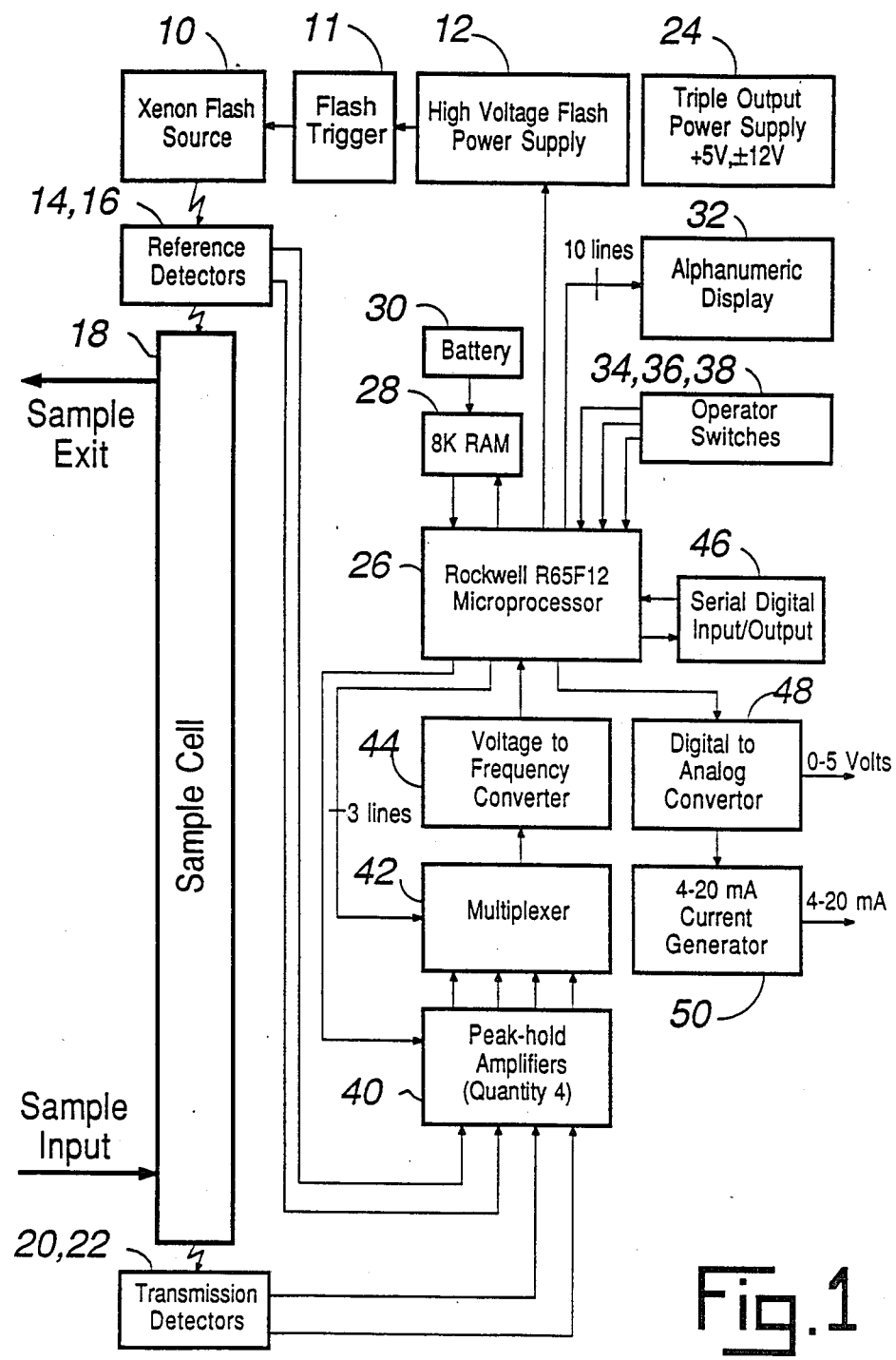
FIG. 1 a block diagram showing the major elements of the apparatus for measuring the organics content of purified water.

A general description of process and apparatus of the invention will first be provided with reference to the block diagram of FIG. 1, followed by a more specific description of the preferred embodiment illustrated by FIGS. 2 through 8.

Referring therefore to FIG. 1, a light source 10 consists of a xenon flash tube which provides periodic pulses of light in reponse to activation by a trigger circuit 11. These pulses contain a relatively uniform distribution of light wavelengths in the range of less than 200 nm to greater than 600 nm, the energy for these flashes being obtained from a 1000 volt D.C. flash power supply 12. The amplitude and spectral distribution of the light pulses are measured by two reference photo-detectors 14 and 16 before the light passes through a sample cell 18, which contains a stationary body of liquid or a continuous flow of liquid, light energy which is not absorbed by the liquid being detected by two transmission photodetectors 20 and 22 at the other end of the cell. The remainder of the components of the apparatus are required to process the signals obtained from the four photodetectors.

A power supply 24 powers all of the computer and signal conditioning circuitry. The apparatus is controlled by a microcomputer 26, which synchronizes the generation of the light pulses and the measurements made by the photodetectors, and also provides the computation necessary to interprete the readings obtained in terms of organics content. The program for the microcomputer is contained in a random access memory 28 which is maintained by its own battery 30. The calculated value of organics content is displayed on an eight character alphanumeric display 32, which is also used to display alarm set points, calibration values, error messages, etc. The operator obtains access to the parameter that is to be displayed by operation of the first of three push button switches 34, 36 and 38, and can then change the displayed parameter by operation of the other two switches. The three switches are therefore labelled "mode", "up" and "down."

Input signals from the two reference detectors 14, 16 and the two transmission detectors 20, 22 are processed sequentially by four peak-hold amplifiers 40, multiplexer 42, and voltage-to-frequency converter 44. Briefly the circuit operates in the following way: the peak-hold amplifiers 40 are reset typically 1 millisecond just before the flash source 10 is fired. When the flash is triggered, the photodetectors 14, 16, 20, 22 produce current peaks which are converted to voltages and stored on respective capacitors. The computer 26 then selects each of the four channels in turn via the multiplexer 42 and places the respective capacitor voltage at the input of the converter 44. The converter 44 provides a frequency between 200 and 100,000 hertz in depedence upon the input voltage which is counted in this embodiment for 30 milliseconds in the microcomputer. At the end of the cycle the four readings are treated as numbers in the computer in the range of 0 to 3000. The algorithm which uses those input numbers will be described later. The remaining parts of the apparatus represented by the remaining blocks in the block diagram comprise a serial digital input/output module 46 providing an input/output to a printer or another computer, a Digital/Analog converter 48 providing a analog output voltage proportional to the display, and a loop-driver module 50 providing a 4–20 mA current proportional to the output voltage from module 48.

Figure 2:
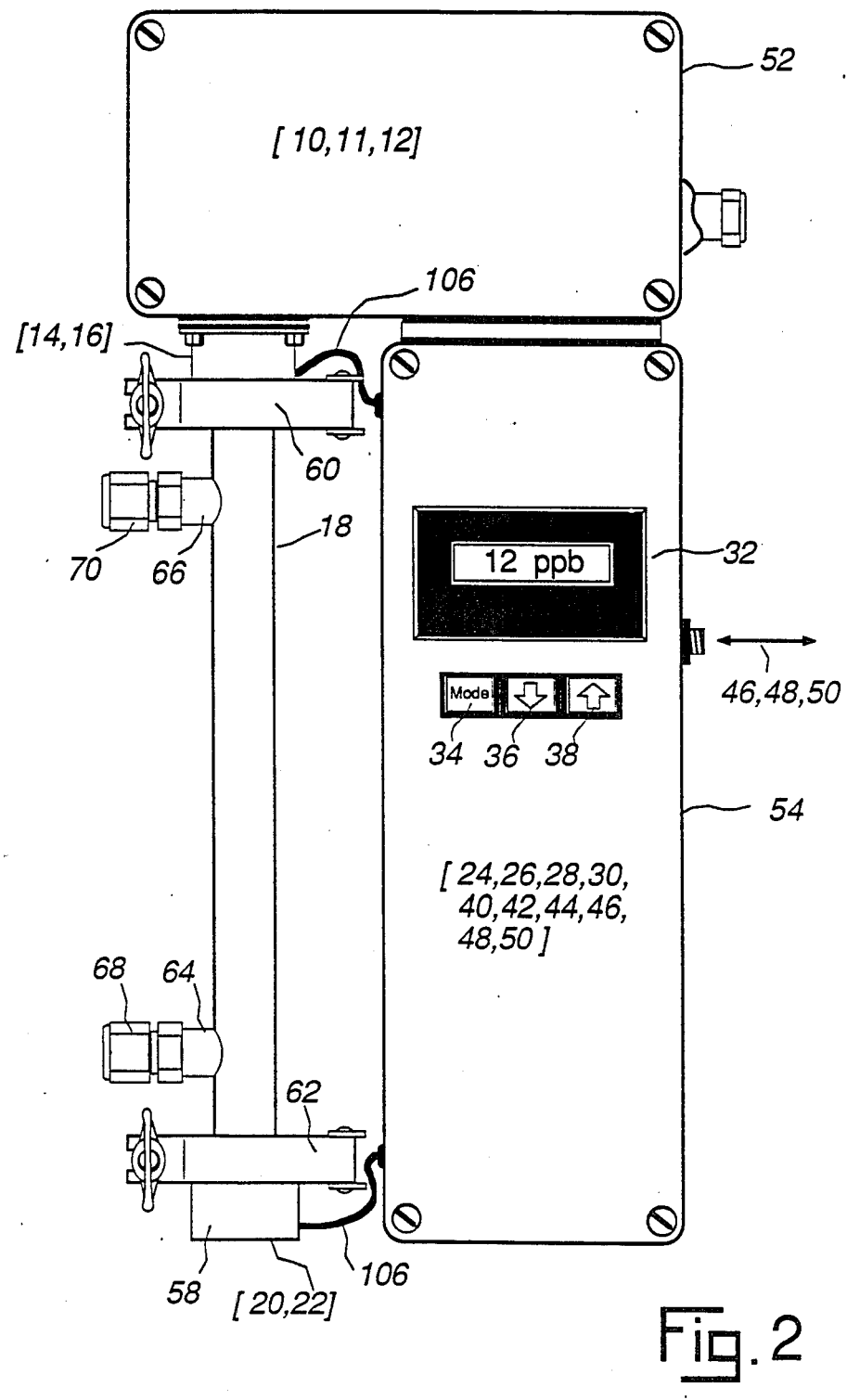
FIG. 2 is a front elevation view of the presently preferred embodiment of the apparatus.

FIG. 2 is an elevation view of the exterior of the preferred embodiment. An upper metal enclosure 52 contains the flash source 10, its trigger circuit 11 and its power supply 12, while a lower metal enclosure 54 contains all the remaining electronics. The separation of the flash electronics from the other electronics in two separate metal enclosures is important in order to reduce electromagnetic interference caused by the flash discharge. An upper enclosure 56 attached to the enclosure 52 contains the reference detectors 14, 16, while a lower enclosure 58 contains the transmission detectors 20, 22, as will be described in more detail below. The sample cell 18 is an elongated, straight metal tube, usually of stainless steel, removably mounted between the two enclosures 56 and 58 by respective clamps 60 and 62, and is provided with a lower inlet 64 and an upper outlet 66 for the water to be examined in the cell, the inlet and outlet being provided with respective fittings 68 and 70 for the connection of hoses thereto.

Figure 3:
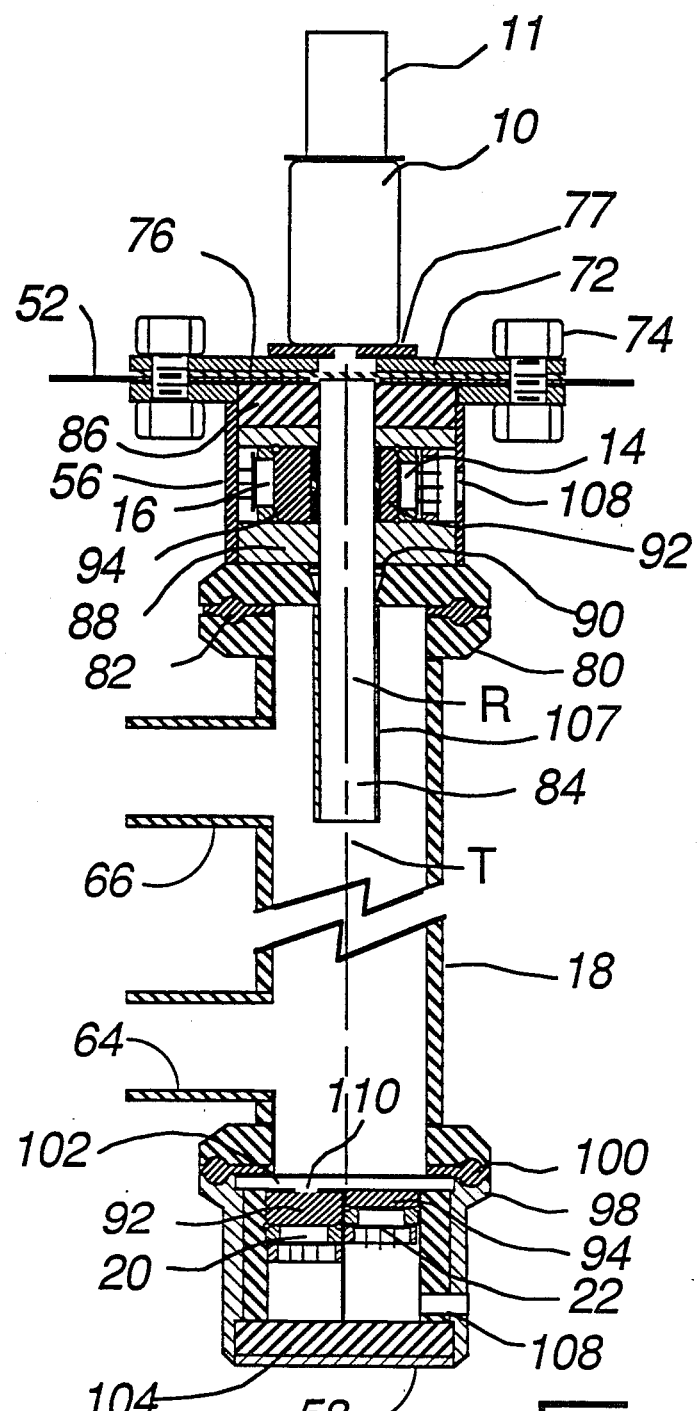
FIG. 3 is a cross-sectional view of a sample cell and associated photodetectors employed in the apparatus of FIGS. 1 and 2.

Referring now to FIG. 3, the flash tube 10 is mounted on a plate 72, which is clamped to the wall of the enclosure 52 by bolts 74 so that a screen 76, of thirty mesh copper or aluminum, is sandwiched between them, the screen providing effective shielding against radio frequency interference from the flash tube. An aperture plate 77 is interposed between the flash tube and the plate 72, the size of the aperture in the plate being adjusted to control the amount of light that passes into the sample tube. The bolts 74 also clamp the enclosure 56 to the enclosure 52. The lower end of the enclosure 56 is provided with a radial flange 78 that matches with a radial flange 80 at the top end of the sample tube 18, the flanges being engaged by the upper clamp 60 (not shown in FIG. 3) and having a gasket 82 sandwiched between them to provide a liquid-tight seal.

The flash tube and the interposed aperture plate are mounted directly over the upper end of a length of quartz rod 84 of cylindrical cross-section, mounted so that its longitudinal axis R is coincident with the longitudinal axis T of the sample tube 18, the rod passing through a support ring 86 of low modulus plastic material, a sensor housing 88, and a ferrule 90 wedged in the flange 78 and providing a liquid-tight seal between the rod and the interior of the sample tube. The rod is formed by snap-cutting it to the required length; there is no requirement without any attempt to improve the flatness or smoothness of the end surface by grinding or polishing. The two reference detectors 14 and 16 are mounted within the housing 88 orthogonal to the rod, the outer surface of which is lightly ground in the area adjacent the detectors, so that a small quantity of the light passing down the rod is refracted toward the detectors. An optical filter 92 with a bandwidth of 10 nm centered around 550 nm (i.e. within the yellow-green visible spectrum) is mounted in front of the detector 14, while another filter 94 with the same bandwidth centered around 220 nm (i.e. within the ultra-violet spectrum) is mounted in front of the other detector 16. It is important that the filters 92 and 94 are mounted in such a way that no light passes around their edges to reach the detectors other than through the filters, and the material used for the sensor housing must also be opaque.

The cell 18 is provided at its lower end with a radial flange 96 that connects to a similar flange 98 on the housing 58, an interposed gasket 100 and the lower clamp 62 to mount the lower housing in water-tight manner on the bottom end of the cell. The interior of the housing 58 is closed by a Suprasil (trade mark) quartz window 102 that allows the passage of both the visible and ultraviolet pulses transmitted by the filters 92 and 94. Transmission photodetector 20 is provided with a transmission filter 92 of the same bandpass characteristic as that in front of the reference detector 14, while transmission detector 22 is provided with a filter 94 of the same characteristic as that in front of the reference detector 16. A pad 104 of low modulus plastic material provides an endwise compression force to ensure a water tight seal. The shielded electrical connections 106 (see FIG. 2) from the four detectors exit the enclosures 56 and 58 through openings 108.

It is important for satisfactory operation of the apparatus that the flow in the sample tube 18 be upward from the inlet to the outlet so that bubbles in the liquid are not trapped in the cell. It will be seen from FIG. 3 that the quartz rod protrudes into the cell a sufficent distance for its lower end to be below the outlet port 66 to ensure that bubbles in the liquid are not trapped on the rod end. The adhesion of bubbles to the side of the rod is inhibited by a tubular sheath 107 of low-friction material (e.g. of "Teflon"-Trade Mark) that fits tightly around it, leaving the lower end exposed. The relation between the rod diameter and the internal diameter of the cell is not important, except it is essential that a straight light path can be ensured between the lower end of the rod and the transmission photodetectors 20 and 22. It is important that the rod 84 be of a material that is suitably transmissive of the light pulse over the range of wavelengths required for the measurements, and in this specific embodiment it is of Suprasil (trade mark) quartz as sold by Heraeus Amersil of Sayreville, N.J. It is of 10 cm (4 in) length and external diameter 10 mm (0.4 in), while the sample tube 18 is of overall length 3 cm (12 in) and 2.5 cm (1 in) internal diameter.

The method and apparatus of the invention utilize the principles of dual wavelength, dual pathlength absorbance measurement to overcome many of the limitations inherent in earlier instruments. The performance is further enhanced through the use of a flash lamp as a relatively small inexpensive intense light source, and a flexible non-optically critical mounting scheme to ensure high sensitivity and robustness. The variablility of a flash source can be significant, both in terms of intensity and spectral character, over both short and long periods, and also because of the possibility of the very intense light pulse causing the passage of extra-spectral light through the filters. An essential feature of an aspect of this invention is the means of detecting such variations in the source, and of compensating for them in the subsequent calculations. Thus, the method of the invention as disclosed herein utilises the two transmission detectors 20 and 22 mounted in such a way as to view the source in an identical manner, while the reference detectors 14 and 16 provide the necessary compensation. An important feature of the invention is the use of a true "white" light source, i.e. of sufficiently uniform output characteristic over the range of wavelengths required. The xenon flash lamp source used in the present embodiment of the invention, supplied by Optikon Corporation Ltd., is specially constructed to emit a reasonably uniform spectrum of light over the band from 180 nm to greater than 600 nm, this feature being implemented by the inclusion of a quartz cover over the flash lamp itself and the use of the quartz window 102 in front of the detectors 20 and 22. This arrangement is in contrast to other measurement systems which use mercury or deuterium lamps, which emit light in the form of discrete spectral lines. The broad spectrum provided by this xenon source allows the method and apparatus of the present invention to be tuned to the response of the compounds of interest by suitable choice of the transmission filters 92 and 94. In addition, more detectors at various wavelengths may be included to provide additional specificity. In order to ensure uniform and stable output from the flash lamp it will usually be operated under optimum conditions; if it is found in practice that the light output is too high for the particular application, then it is preferred to use a lamp of lower output, also operated under optimum conditions, or to control the intensity of the pulse by some external means, such as the aperture plate 77. It may also be found necessary to provide individual attenuation of the portions of the pulse that are applied to the individual detectors, in order to ensure that they are operated within their optimum ranges of light input intensity, and preferably this also is done externally by means such as an individually-calibrated aperture plate. The most likely candidate for such control is the transmission detector 20 for the visible spectrum, and in this embodiment this is provided with an aperture plate 110.

The physical arrangement of the invention, giving the ability to separate the light transmission detectors from the source of light, permits the apparatus to be mounted in a wide variety of industrial piping arrangements for on site sampling and continuous monitoring of water quality. The apparatus normally is used in a water treatment process as one of the final elements in a train of treatment units, and usually will be mounted in the purified water stream, or as a sample by-pass thereto, close to the point of use of the water. Successive measurements can be made at any suitable interval down to as small as 10 seconds, the measuring circuit being arranged that if the level of the selected organics measured exceeds a maximum, or is below a minimum, then an audible and/or visible alarm signal is issued. Continuous indication of the organic content can be displayed and/or recorded.

The walls of the chamber 18 should be completely opaque either by use of opaque material or by the provision of an opaque coating or coatings. The ultra-violet light is the "analysis" medium and is selected to be the wavelength that is most strongly absorbed by the components of interest; let its intensity be represented as Ms. The reference wavelength used to compensate for non-spectral variations in the optical system is chosen for maximum transmission by the sample; it is represented by Rs. The reference measurements that are used to monitor variations in the source are represented respectively by Mc and Rc. The four separate detectors produce electrical outputs each of which is proportional to the energy that is focussed on it; let them be represented by these integers. The concentration of the component of interest in the sample C is found from application of Beer's Law:

$$C = K \cdot \log 10 \cdot \frac{Rs \cdot Mc}{Rc \cdot Ms}$$

which confirms that neither sample cell contamination nor variation in source intensity should affect the value of C.

Lambert's law of absorption states that each layer of equal thickness absorbs an equal fraction of the light which traverses it, so that the sensitivity of the measurements will increase with the length of the sample light path; thus provided the light is sufficiently intense and the concentration of the compounds of interest is sufficiently low, the detection limit can be increased simply by increasing the length of the sample chamber, and this can be done very easily with the apparatus of the invention, since it is the length of the tube 18 that determines the path length. If the apparatus is to be used with a moving sample it is preferred that the liquid flow rate in the sample cell is above about 2 meters per second in order to eliminate adhesence of residual bubbles to the cell surfaces.

Thus, the invention takes advantage of the fact that most organic compounds absorb ultraviolet light to some degree, and that at low concentrations (below 1 ppm) this absorption is directly related to their concentration. Correction is provided for interference in the transmission measurement stream due, for example, to particulates in the sample, fouling of the optical surfaces by the sample, and bubbles in the sample, by the simultaneous reading of a transmission from the same source in the visible portion of the spectrum. The readings that are thus obtained are further corrected by obtaining readings from the pair of reference sensors. The outputs of these two reference sensors can therefore be used to compensate for inevitable variations in the output of the flash tube, which can be as much as 10%, and which can be accomodated by this invention. Thus, the reference signal in each of the two spectrum portions can be used to "normalise" the sample signal. It is of course possible to use a different form of light source which is pulsed by use of a mechanical shutter, but the xenon flash light source that preferably is employed is compact, relatively inexpensive and able to develop effective power output of as much as 500,000 watts, which are difficult to achieve with other types of light source. A limitation to the method and apparatus is that the technique is relatively insensitive to some compounds that may be of interest, although this can be mitigated to some extent by suitable choice of the filters 92 and 94 to suit the compound or compounds to be detected. The sensitivity can be pre-determined by measurement of the A/TOC ratios in that compounds which have a ratio of less than 0.1 can only be detected effectively in isolation. An example of a very high ratio compound is hexachlorobutadiene (2.24), while a low ratio compound is toluene (0.0343).

Since the selected preferred wave lengths of operation are 220 nm and 550 nm, the transmission media must be as completely uniformly transparent in that range as possible. It is found that ordinary optical grade quartz materials have increased absorbtion at wave lengths less than 300 nm, and the selected material, which is a synthetic quartz, solves this problem since its absorption spectrum is virtually non-existent over the range of interest.

Among the advantages of the use of a xenon flash is the fact that it behaves as a combination of both ultraviolet and visible light source, while the concentration of the light energy into a few microseconds permits the use of low cost semiconductor photodetectors, rather than the more complex and costly photomultipliers that would otherwise be required. The fact that the light is emitted as a very high intensity, short length pulse also increases the signal to noise ratio by several orders of magnitude. The pulse rate can be very readily adjusted to suit the processing environment and can be extended from the above-mentioned period of 10 seconds, which for this specific apparatus is the shortest practical time, to whatever period is required for adequate control of the process. More frequent measurements are also possible, up to several flashes per second, by choice of a suitable lamp and its power supply. The use of the electronic flash also dictates the choice of the photodetectors, since they must be sensitive to light at 220 nm as well as 550 nm. Moreover, they should have a response of about one volt/microsecond or better and be relatively small in size. The filters that were employed are stock which are available from Microcoatings Inc. of Westford, Mass. As explained above, a problem can arise if too much light is applied to the photodetectors, since this would saturate them, while with too little light the signal that is produced would be buried in the ambient noise; this is prevented by the use of suitable apertures as discussed above.

The selection of "analysis" ultraviolet light in the 200–220 nm band was based upon a finding that this would be the frequency band adequately sensitive to most of the compounds of interest, and scans to test samples showed that this band has excellent sensitivity of contaminants of principle interest in water treatment processes. The actual band employed will be dictated by the specific contaminant or combination of contaminants of interest, and the availability of suitable band pass filters. The filter that was actually employed had a band pass of 10 nm centered on 217 nm. This means that the analyser is also sensitive to inorganic compounds such as nitrogen or bromine containing compounds (i.e. ammonia, chloramines, bromoform) as well as a broad range of organic compounds. Selection of the value of 220 nm is believed to be unconventional, and is due to the fact that this particular absorbent band sits on the steep shoulder of an increasingly absorbent peak. Normal considerations would dictate that the selected band should straddle a peak, or at least be sited on a flat part of the curve. However, it has been found that in this particular field the flat portion is relatively quite insensitive and not as universal as the selected frequency. It is also found that the 550 nm visible light employed to generate a correction signal proved to be suitably non-sensitive to compounds of interest. However, this band could be moved to a lesser wave length with the result of a smaller scattering correction being required (i.e. a better back-ground).

The operating range of the instrument is readily adjustable by a choice of the measurement parameters, as will become apparent. The normal detection limit of this embodiment is 10 ppb while the maximum upper limit is considered at the present time to be 2.5 ppm. The sample cell 18 may range in length from 1.0 cm to 100 cm (0.4 inch to 40 inches) and in diameter from 2.5 cm to 15 cm (1 inch to 6 inches); the operating pressure which can be accommodated depends of course on the effectiveness of the sealing that is provided, and can be as high as 1MPa (150 psi).

Figure 4:
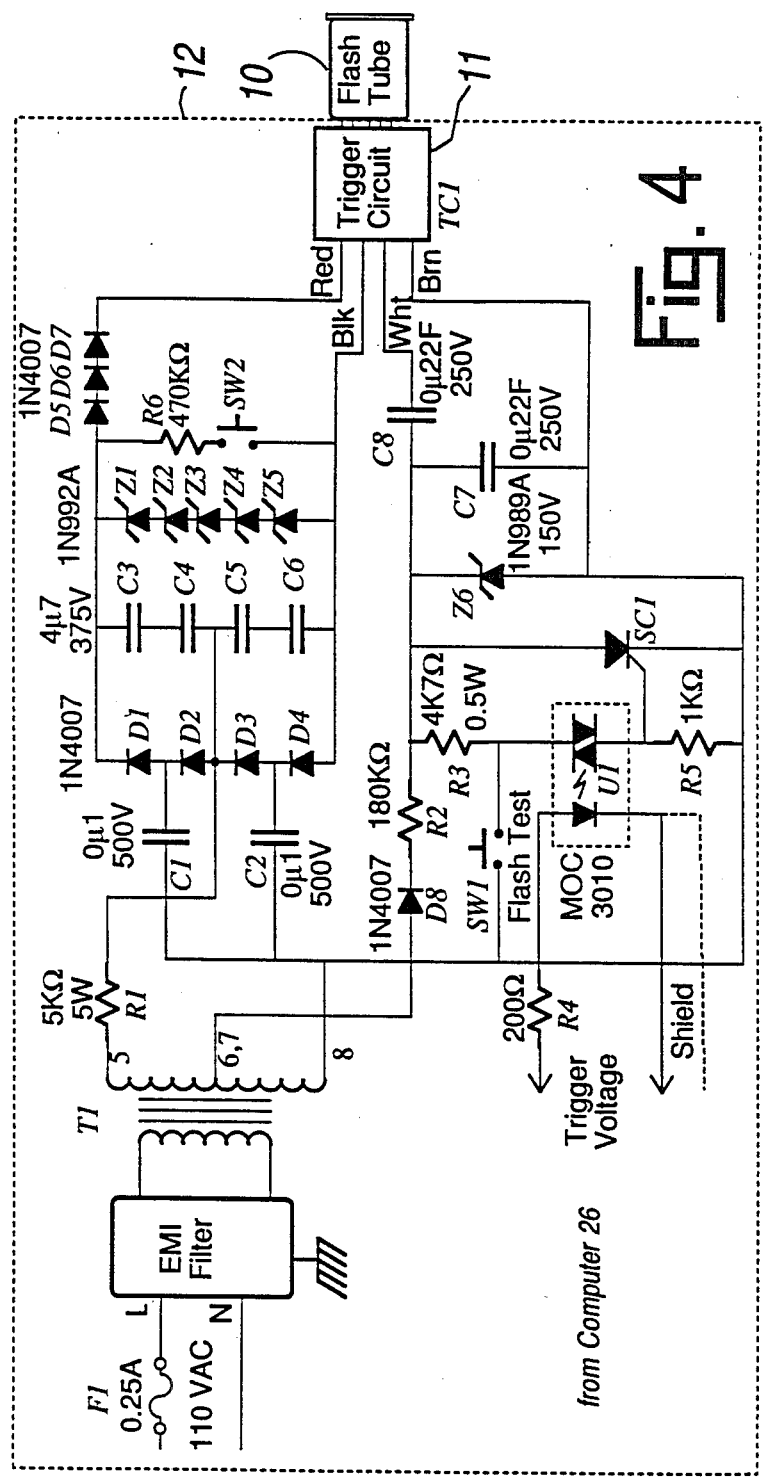
FIG. 4 is a schematic diagram of the power supply for an intermittent light source employed in the apparatus.

FIG. 4 is a schematic circuit diagram of the flash power supply of this embodiment. The supply includes clamping diodes Z1 through Z5 to ensure a consistent amount of charge is available on capacitors C3 to C6 for supply to the flash tube. An optically-coupled photodiode unit U1 provides isolation between the lamp circuit and the computer-generated flash trigger circuitry.

Figure 5:
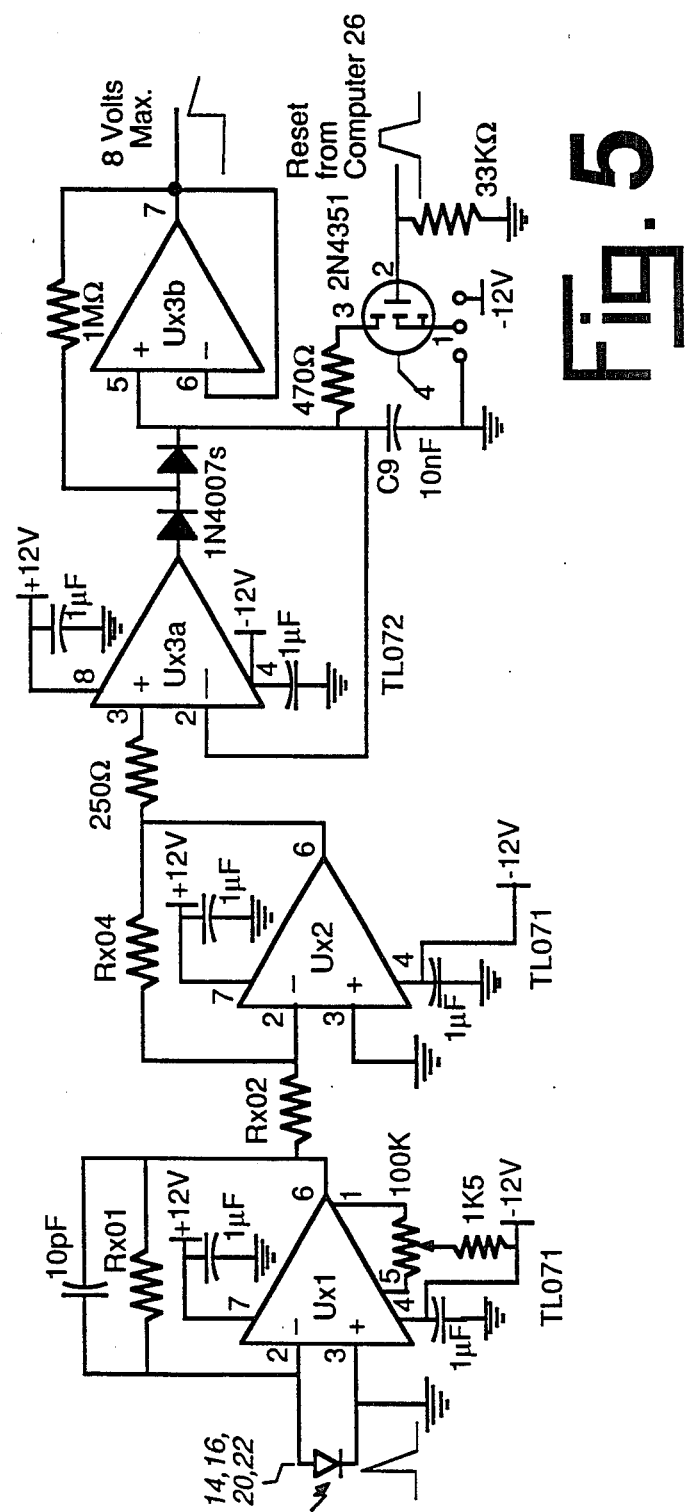
FIG. 5 is an electronic schematic diagram of a peak-hold amplifier employed in the apparatus.

FIG. 5 shows a suitable "peak-hold" circuit for acquiring and holding the maximum value of the pulse from each photodetector 14, 16, 20 and 22 as it receives its respective light pulse originating from the source 10. Four such amplifier trains are provided, one for each detector, that illustrated being, for example, for the photodetector 14; each amplifier requires individual values for gain control resistors RX01, RX02, RX04 and RX05. The operation of the circuit is that amplifier Ux1 converts the current pulse provided by the photodetector to a voltage and provides some gain; amplifier Ux2 provides an additional gain stage; amplifiers Ux3 and Ux3b and their associated components comprise a resettable peak hold detector. This arrangement was found to retain the voltage on the polystyrene capacitor C9 with a droop of only a few millivolts per second, it being important that the droop be consistent over the range of operating conditions. The transistor 2N4351 is pulsed to zero the peak hold circuit by a reset pulse from microprocessor 26 immediately prior to flashing the xenon lamp 10. The lay-out of these peak-hold circuits on the printed circuit board is important, and it is necessary to include a ground plane layer to minimize electronic noise interference. In the preferred embodiment the peak-hold amplifiers are mounted at the lower end of the lower electronics housing 54 to maximize the distance from the interference source, namely the flash unit 10.

Figure 6:
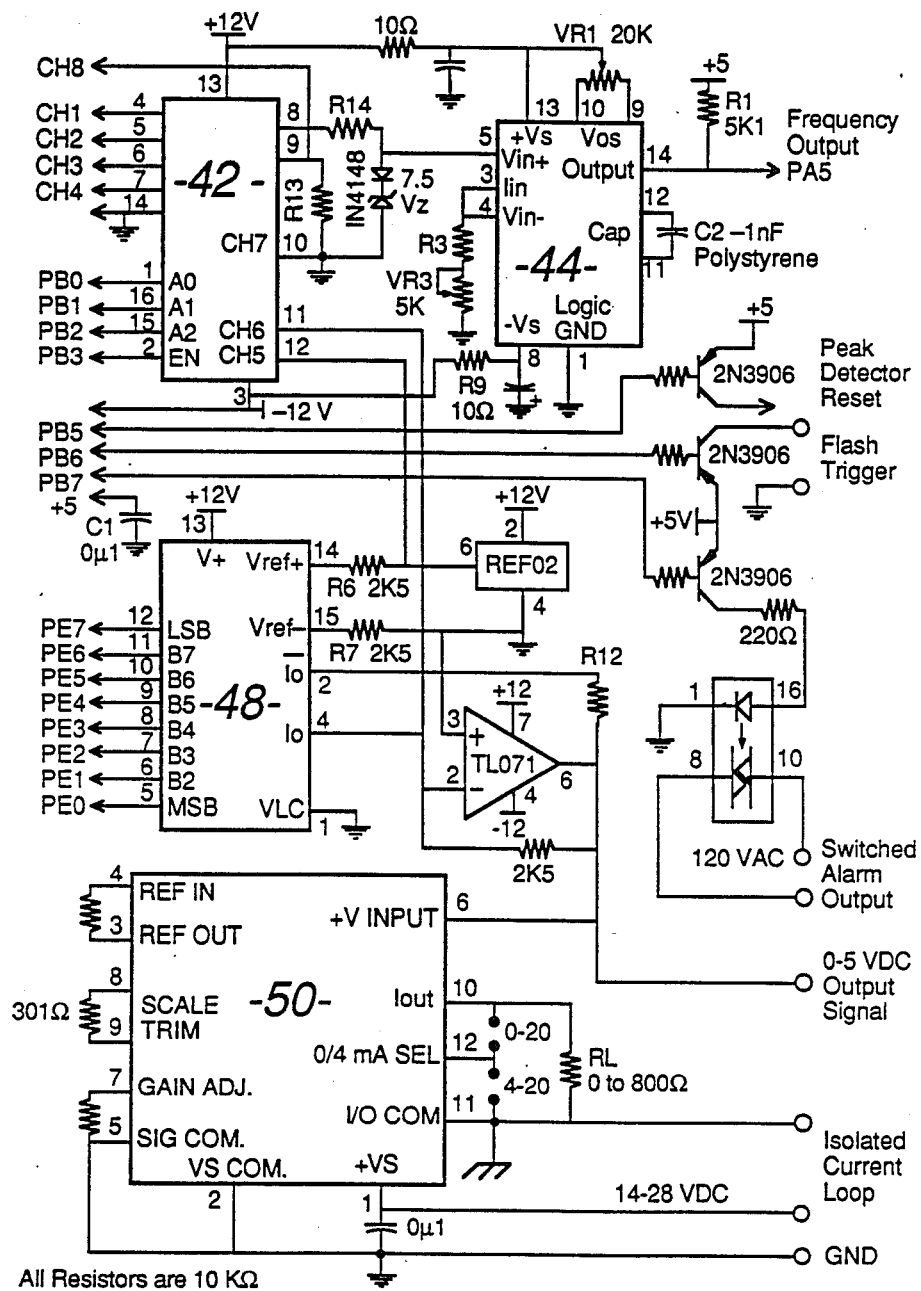
FIG. 6 is an electronic schematic diagram of other interface circuits between the peak-hold amplifiers and a microcomputer, current loop interface, and flash trigger.

FIG. 6 shows the interfacing of the remaining electronics to and from the micro-computer 26.

In FIG. 7 the same reference numbers are used whenever possible for the same parts as in FIGS. 1-6. The drawing shows another embodiment of the invention and illustrates the manner in which it can be applied to an existing pipe 18 though which a process stream passes. This is accomplished by attaching elbows 112 and 114 into the pipe and then mounting the enclosures 56 and 58 respectively on the elbows, the two enclosures being aligned so that the axes R and T coincide. This embodiment also illustrates the possibility of employing three different ultraviolet transmission cells 20 and one optical transmission cell 22, which are disposed side by side in plan as shown in FIG. 7a. Such an arrangement increases the number of absorbance bands measured and can potentially increase the range of compounds that are detectable by this method. Alternatively, or in addition, it makes it possible to increase the specificity of the measurement to a compound or a group of compounds, the choice being a function of the data conversion algorithm. An additional train of electronics, as in FIG. 5, is required for each additional detector. Suitable additional frequencies are, for example, 276 nm and 300 nm.

The apparatus and methods described above as specific preferred embodiments of the invention were developed for measurement of the organics content in water, but the invention is also applicable generally to the measurement of the concentration of light-absorbable components dissolved in sufficiently transparent, non-aqueous liquids. A commercial example of such an application would be for the determination of the concentration of a phthalate in ethyl alcohol.

The control program for the invention is given in FIG. 8. In this embodiment the micro-computer employed is a model NMIX-0012 single board of New Micros Inc., Grand Prairie, Tex., which utilizes a Rockwell R65F12 micro-processor programmable in FORTH language. The program is therefore written in FORTH; in particular it is written in RSC-FORTH, which is a special implementation of FORTH for the Rockwell R65F12. By way of explanation for those knowledgeable in the art of programming, but not FORTH, a suitable reference book is called *STARTING FORTH* by Leo Brodie. For those not interested in the commands within the program, but rather the structure, it should be noted that FORTH is hierarchical. That is, the lowest level words (subroutines) are defined at the beginning of the program.

Very briefly, some of the syntax is as follows: ":" indicates the beginning of a new definition and ";" indicates the end of a definition. "@" means get the value of the just named variable and "!" means store to the just named variable. An understanding of these basic shortforms gives the person having the required knowledge of programming techniques enough information to understand the basic flow of the program. For more, see Brodie or the RSC-FORTH programming manual.

What now follows is a brief tour of the major elements of the code. References are given by word-name/page/line. For example TIMER2/1/5 refers to the variable TIMER2 first referenced on Page 1 and Line 5 of the program listing. The first 38 lines on page 1 set up a basic interrupt driven set of timers which are generally used throughout the rest of the program. The four timers are identical and run with 1/100th of a second resolution. IRQINIT/1/35 is used to enable interrupts and initialize the timers to 0.

Trigger/2/5 is the I/O assignment for the flash trigger circuit. The word TTRIG/3/25 is used to pulse the flash. RSET/2/7 is the I/O assignment for the peak-hold amplifier reset circuit.

The method of conversion from analog to digital signals is by the voltage to frequency converter 44. The code of Page 2, lines 1 to 36 enables the sampling of the various analog channels and the concentration calculations require the use of logarithms which are not implemented in the FORTH kernel. Page 6/Line 1 to Page 8/Line 6 implement both base 2 and base 10 logarithms.

Finally the code given on pages 8/Line 8 to page 9/Line 5 implements the equations necessary to calculate absorbance and concentration from the raw data. The word AVG/9/10 calculates a weighted average over the last six samples according to a predetermined lambda filter factor.

The word RUN/9/16 causes the application to run and perform all the necessary functions encompassed by the previously defined words. Specifically it initializes the LCD display HDINIT/9/17; displays the start-up message ZEN/9/18; initializes the interrupt timers IRQINIT/9/19; and then begins to loop until the power is turned off, or the operator stops the process by pressing a key on a terminal connected to the RS-232 port.

The main loop Page 9/lines 20 to 29, waits 10 seconds (10S?/9/21); resets the peak-hold amplifiers, triggers the flash and gets four new sensor values (SENS-read/9/22); calculates the new absorbance (ABSO-EB1/9/23); new concentration (CALCALC/9/24); new average (AVG/9/25); and displays the new estimated TOC (.TOC/9/25). Then the program waits another 10 seconds, and so on for as long as is required.

I claim:

1. Apparatus for determining the concentration of ultra-violet light absorbing organic substances in a liquid sample, the apparatus comprising:
   a sample chamber for the reception of the liquid sample and having a longitudinal axis;
   a light source positioned for its light to enter the sample chamber and when energised emitting light in two spaced spectrum portions, one of which is in the ultra-violet region and the other of which is in the visible region;
   two transmission photodetectors positioned to receive light from the source that has passed through the sample chamber and the liquid sample along the longitudinal axis, one of the photodetectors being responsive to light in the said ultra-violet region and the other being responsive to light in the said visible region, the two photodetectors generating respective transmission ultra-violet and visible electric signals;
   two reference photodetectors positioned to receive light from the source prior to it passing through the sample chamber, one of the photodetectors being responsive to light in the said ultra-violet region and the other being responsive to light in the said visible region, the two photodetectors generating respective reference ultra-violet and visible electric signals; and
   circuit means combining said electric signals to produce an output electric signal representative of the concentration of ultra-violet light absorbing substances in the liquid sample, in which the reference signals are employed to correct the transmission electric signal for variations in the light source light output, and in which the transmission visible electric signal is employed to corret the transmission ultra-violet electric signal for variations in the light transmission path.

2. Apparatus as claimed in claim 1, wherein the light source is an electrically-triggered electronic flash lamp.

3. Apparatus as claimed in claim 2, wherein the light output of the flash lamp is discharged into one end of a transparent rod having a longitudinal axis at least parallel to the longitudinal axis of the sample chamber, the rod protruding into the sample chamber.

4. Apparatus as claimed in claim 1, wherein each photodetector is provided with a narrow band-pass optical filter of the portion of the spectrum for which the photodetector is to be responsive.

5. Apparatus as claimed in claim 2, wherein said circuit means includes microcomputer control means for synchronising the triggering of the flash lamp and the subsequent combining of the said electric signals from the photodetectors to produce the said output electric signal.

6. Apparatus as claimed in claim 5, wherein said circuit means includes a plurality of peak-hold amplifiers equal in number to the number of photodetector output signals, and wherein said peak-hold amplifiers are reset by the microcomputer in synchronism with the operation of said light source.

7. Apparatus as claimed in claim 1, wherein the sample chamber is disposed with the longitudinal axis vertical and has a lower inlet thereto and an upper outlet therefrom, and including means for introducing the liquid sample into the sample chamber to provide for a continuous flow of said liquid upward in the chamber from the inlet to the outlet.

8. Apparatus according to claim 5, wherein the reference and transmission signals are analog signals, the microcomputer control means includes a digital microprocessor means, and there is provided an analog to digital converter means interposed between said photodetectors and said micro-processor means for converting said analog signals into corresponding digital signals for processing by said micro-processor means.

9. Apparatus as claimed in claim 8, wherein the concentration value determined by the digital microprocessor means is re-converted from digital to analog form by means of a digital to analog converter interconnected between said digital micro-processor means and an analog output device.

10. A method for determining the concentration of ultra-violet light absorbing organic substances in a liquid sample, the method comprising the steps of:
   a. providing a sample chamber for the reception of the liquid sample and having a longitudinal axis;
   b. positioning a light source for its light to enter the sample chamber and when energised emit light in two spaced spectrum portions, one of which is in the ultra-violet region and the other of which is in the visible region;
   c. positioning two transmission photodetectors to receive light from the source that has passed through the sample chamber and the liquid sample along the longitudinal axis, one of the photodetectors being responsive to light in the said ultra-violet region and the other being responsive to light in the said visible region, the two photodetectors generating respective transmission ultra-violet and visible electric signals;
   d. positioning two reference photodetectors to receive light from the source prior to it passing through the sample chamber, one of the photodetectors being responsive to light in the said ultra-violet region and the other being responsive to light in the said visible region, the two photodetectors generating respective reference ultra-violet and visible electric signals; and
   e. supplying the said electric signals to circuit means which combine them to produce an output electric signal representative of the concentration of ultra-violet light absorbing substances in the liquid sample, in which the reference signals are employed to correct the transmission electric signal for variations in the light source light output, and in which the transmission visible electric signal is employed to correct the transmission ultra-violet electric signal for variations in the light transmission path.

11. A method as claimed in claim 10, wherein the light source is an electrically-triggered electronic flash lamp.

12. A method as claimed in claim 10, wherein the light output of the flash lamp is discharged into one end of a transparent rod having a longitudinal axis at least parallel to the longitudinal axis of the sample chamber, the rod protruding into the sample chamber.

13. A method as claimed in claim 10, wherein each photodetector is provided with a narrow band-pass optical filter of the portion of the spectrum for which the photodetector is to be responsive.

14. A method as claimed in claim 11, wherein said circuit means includes microcomputer control means synchronising the triggering of the flash lamp and the subsequent combining of the said electric signals from the photodetectors to produce the said output electric signal.

15. A method as claimed in claim 14, wherein said circuit means includes a plurality of peak-hold amplifiers equal in number to the number of photodetector output signals, and wherein said peak-hold amplifiers are reset by the microcomputer in synchronism with the operation of said light source.

16. A method as claimed in claim 10, wherein the sample chamber is disposed with the longitudinal axis vertical and has a lower inlet thereto and an upper outlet therefrom, and including means for introducing the liquid sample into the sample chamber to provide for a continuous flow of said liquid upward in the chamber from the inlet to the outlet.

17. A method according to claim 14, wherein the reference and transmission signals are analog signals, the microcomputer control means includes a digital micro-processor means, and there is provided an analog to digital converter means interposed between said photodetectors and said micro-processor means for converting said analog signals into corresponding digital signals for processing by said micro-processor means.

18. A method as claimed in claim 17, wherein the concentration value determined by the digital microprocessor means is re-converted from digital to analog form by means of a digital to analog converter interconnected between said digital micro-processor means and an analog output device.

* * * * *